US012783963B1

(12) United States Patent
Wittenauer et al.

(10) Patent No.: US 12,783,963 B1
(45) Date of Patent: Nov. 3, 2026

(54) COMPUTER-BASED SYSTEMS AND METHODS FOR CONFIGURATION-DRIVEN CONTINUOUS TRAINING OF LARGE LANGUAGE MODELS IN AUTONOMOUS CODING

(71) Applicant: R1 RCM Inc., Murray, UT (US)

(72) Inventors: Jason Wittenauer, Round Rock, TX (US); Shelby Lee, Lafayette, CA (US); Justin Silva, Milwaukie, OR (US); Marigrace Ferrill, Charlotte, NC (US); Nikita Rubocki, Boise, ID (US); Bailey Hsu, Draper, UT (US); Johanna Marcelia, Boise, ID (US); Kelsey Ryan, New York, NY (US); Lexi Van Metre, New York, NY (US); Eric Faust, Seattle, WA (US); Heather Armstrong, Suwanee, GA (US); Raquel Freeman, Washington, DC (US); Saathy Vangati, San Francisco, CA (US); Scott Lynch, San Rafael, CA (US); Richa Jain, Sammamish, WA (US)

(73) Assignee: R1 RCM INC., Murray, UT (US)

( * ) Notice: Subject to any disclaimer, the term of this patent is extended or adjusted under 35 U.S.C. 154(b) by 0 days.

(21) Appl. No.: 19/549,516

(22) Filed: Feb. 25, 2026

(51) Int. Cl.
*G06N 20/00* (2019.01)
*G16H 10/60* (2018.01)

(52) U.S. Cl.
CPC ............ *G06N 20/00* (2019.01); *G16H 10/60* (2018.01)

(58) Field of Classification Search
None
See application file for complete search history.

(56) References Cited

U.S. PATENT DOCUMENTS 6,985,898 B1 * 1/2006 Ripley .................. G06F 16/338 707/999.005
2004/0162894 A1 * 8/2004 Griffin ...................... G06F 9/50 709/223

(Continued)

*Primary Examiner* — Ryan Barrett
(74) *Attorney, Agent, or Firm* — Greenberg Traurig, LLP

(57) ABSTRACT

A system and method for configuration-driven continuous training of large language models in autonomous medical coding normalize multi-source electronic health data into provenance-preserving, specialty-aware schemas and provide schema-mapped context to a configurable multi-stage reasoning pipeline to generate candidate code bundles including evaluation and management levels, procedure codes, modifiers, diagnosis codes, and linkages. A ruleset-based validation layer enforces bundling, modifier applicability, and payer policies, and emits machine-readable explanations with rule identifiers, evidence references, and pass/fail indicators. A telemetry-enabled user interface captures approvals, rejections, edits, and rationales, which are consolidated with validation results into provenance-tracked training examples via a trust- or quality-weighted consensus. Signals from reasoning outputs, validation checks, user interactions, and downstream outcomes are fused to produce continuous learning signals that update prompt templates and output ranking parameters through configuration rollouts-without redeploying base models. The approach improves accuracy, robustness, explainability, and auditability for scalable EHR integration.

20 Claims, 9 Drawing Sheets

Context-Aware Data Mapping Framework for Autonomous Coding

(56) References Cited

U.S. PATENT DOCUMENTS

| | | | | |
|---|---|---|---|---|
| 2006/0015431 | A1* | 1/2006 | Bugaj | G06F 16/10 705/35 |
| 2008/0027930 | A1* | 1/2008 | Bohannon | G06F 16/20 |
| 2008/0168109 | A1* | 7/2008 | Gaurav | G06F 16/213 707/999.203 |
| 2009/0030862 | A1* | 1/2009 | King | G06F 18/214 706/45 |
| 2009/0112916 | A1* | 4/2009 | Stuhec | G06Q 10/10 707/999.102 |
| 2011/0219450 | A1* | 9/2011 | McDougal | G06F 21/56 726/23 |
| 2012/0306853 | A1* | 12/2012 | Wright | G06T 19/20 345/589 |
| 2012/0310868 | A1* | 12/2012 | Martins | G06F 16/313 706/12 |
| 2014/0172618 | A1* | 6/2014 | Lewis | G06Q 30/0611 705/26.4 |
| 2014/0215344 | A1* | 7/2014 | Ligman | H04L 67/10 715/736 |
| 2015/0095016 | A1* | 4/2015 | Karres | G16H 10/20 704/9 |
| 2016/0019351 | A1* | 1/2016 | Ober, Jr. | G06F 16/367 705/3 |
| 2016/0239617 | A1* | 8/2016 | Farooq | G16H 10/60 |
| 2016/0350486 | A1* | 12/2016 | Plunkett | G16H 10/60 |
| 2016/0350487 | A1* | 12/2016 | Plunkett | G16H 50/20 |
| 2018/0032678 | A1* | 2/2018 | Dandala | G16H 50/70 |
| 2018/0032679 | A1* | 2/2018 | Dandala | G06F 3/0482 |
| 2018/0068083 | A1* | 3/2018 | Cohen | G16H 50/30 |
| 2019/0098039 | A1* | 3/2019 | Gates | G16H 50/20 |
| 2019/0189253 | A1* | 6/2019 | Kartoun | G16H 50/70 |
| 2020/0334270 | A1* | 10/2020 | Vasireddy | G06F 16/214 |
| 2021/0117662 | A1* | 4/2021 | Wang | G06Q 10/40 |
| 2022/0188181 | A1* | 6/2022 | Saha | G06N 3/09 |
| 2022/0404153 | A1* | 12/2022 | Meng | G06N 3/045 |
| 2024/0105292 | A1* | 3/2024 | Theodorou | G16H 10/60 |
| 2024/0331434 | A1* | 10/2024 | Sabapathy | G06V 30/416 |
| 2025/0157637 | A1* | 5/2025 | Barrow | G16H 10/60 |
| 2025/0225371 | A1* | 7/2025 | Yu | G06N 3/045 |
| 2025/0384013 | A1* | 12/2025 | Pal | G06F 16/1748 |

* cited by examiner

Layered Prompt-Based Autonomous Coding System

COMPUTER-BASED SYSTEMS AND METHODS FOR CONFIGURATION-DRIVEN CONTINUOUS TRAINING OF LARGE LANGUAGE MODELS IN AUTONOMOUS CODING

FIELD OF TECHNOLOGY

The present disclosure generally relates to computer-based systems and methods for configuration-driven continuous training of large language models in autonomous coding.

BACKGROUND OF TECHNOLOGY

Medical coding translates clinical documentation into standardized procedure and diagnosis codes used across healthcare information systems. Conventional approaches frequently depend on manual review or static natural language processing models that require periodic, large-scale retraining to accommodate specialty-specific documentation and evolving coding standards. Retrieval methods based on keyword matching or rigid rules often fail to capture clinical context, leading to inconsistent code selection. Additionally, constructing high-quality labeled datasets remains costly and slow, limiting model improvement cycles. Existing systems also lack tightly integrated mechanisms to incorporate real-time technical feedback signals from users and automated validators, which leads to model drift and reduced reliability.

SUMMARY

In at least some embodiments, a computer-based method may include processing electronic health data by receiving, by at least one processor, electronic health data and session-level event records from multiple electronic resources, where the electronic health data includes structured record data and unstructured documentation text. The method may further include normalizing, by the at least one processor, the electronic health data and session-level event records into a provenance-preserving schema that retains source lineage and includes specialty-aware context metadata. The method may provide, by the at least one processor, one or more schema-mapped context records, including the specialty-aware context metadata, to a multi-stage reasoning pipeline implemented with at least one machine learning model to generate candidate coding outputs. The method may validate, by the at least one processor, the candidate coding outputs using ruleset-based verification to produce validation results that include verified outputs and validation rationale objects, where the validation rationale objects may include rule identifiers, evidence references, and pass/fail indicators. The method may augment, by the at least one processor, a user interface with telemetry and event logging to capture user interaction data associated with candidate and verified outputs. The method may generate, by the at least one processor, provenance-tracked training examples by consolidating user interaction data and validation results via a weighted adjudication mechanism that aggregates inputs according to role-based and quality-based weights to select ground-truth outcomes. The method may iteratively fuse, by the at least one processor, signals from the reasoning pipeline, validation checks, user interaction data, training examples, and downstream operational outcomes to produce continuous learning signals, and may update configuration data-including prompt templates and output ranking parameters-based on those signals and training examples while deployed base models remain unchanged.

In at least some embodiments, a computer-based system may include at least one memory for storing instructions and at least one processor in communication with the at least one memory. The at least one processor may be configured to execute instructions to receive electronic health data and session-level event records from multiple electronic resources, where the electronic health data includes structured record data and unstructured documentation text. The processor may normalize the electronic health data and session-level event records into a provenance-preserving schema that retains source lineage and includes specialty-aware context metadata. The processor may provide one or more schema-mapped context records, including the specialty-aware context metadata, to a multi-stage reasoning pipeline implemented with at least one machine learning model to generate candidate coding outputs. The processor may validate the candidate coding outputs using ruleset-based verification to produce validation results that include verified outputs and validation rationale objects, where the validation rationale objects may include rule identifiers, evidence references, and pass/fail indicators. The processor may augment a user interface with telemetry and event logging to capture user interaction data associated with candidate and verified outputs. The processor may generate provenance-tracked training examples by consolidating user interaction data and validation results via a weighted adjudication mechanism that aggregates inputs according to role-based and quality-based weights to select ground-truth outcomes. The processor may iteratively fuse signals from the reasoning pipeline, validation checks, user interaction data, training examples, and downstream operational outcomes to produce continuous learning signals, and may update configuration data—including prompt templates and output ranking parameters—based on those signals and training examples while deployed base models remain unchanged.

In at least some embodiments, algorithms described herein may be performed by a processor, such as the at least one processor described in the system and method embodiments herein below.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION

Figure 1:
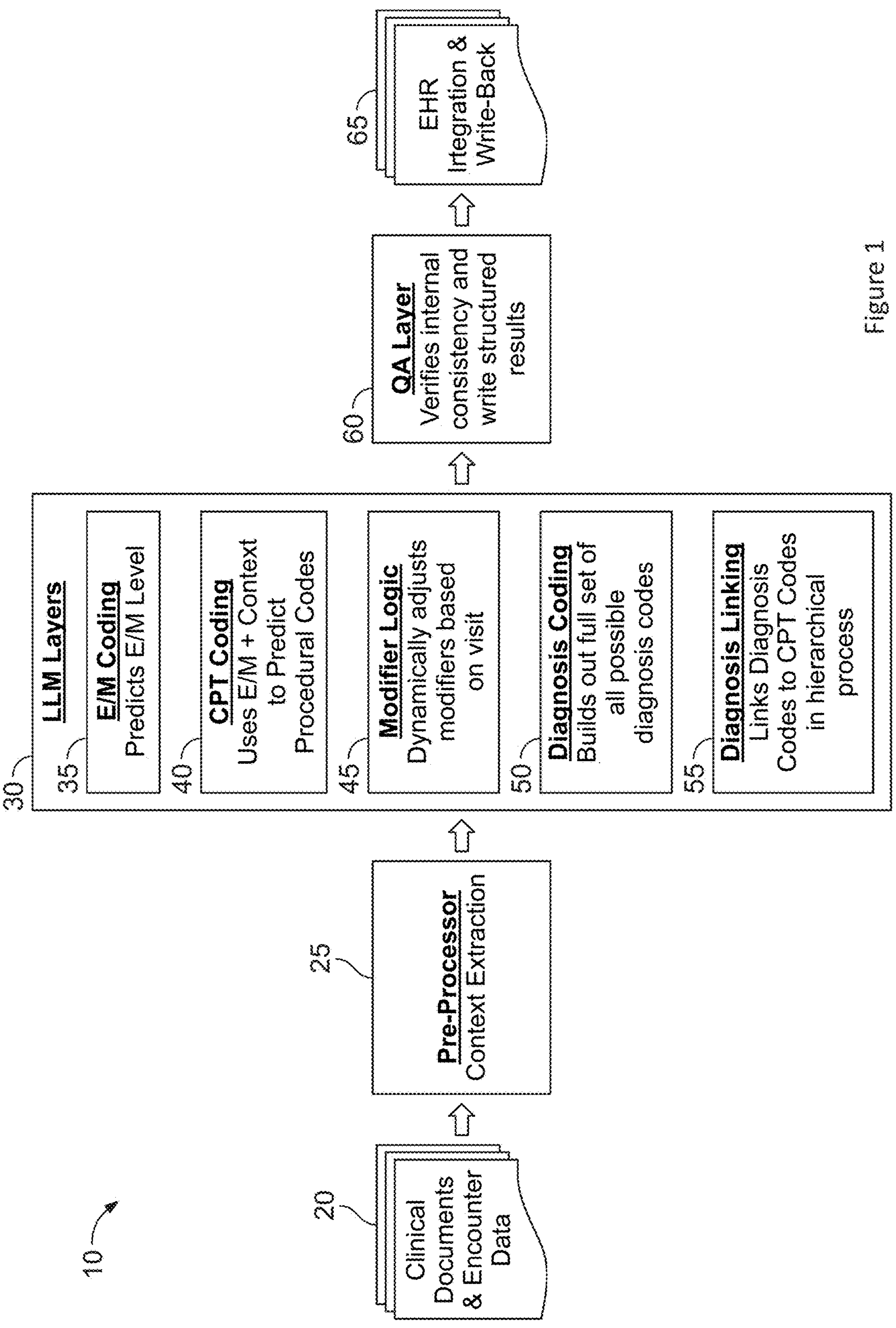
FIG. 1 illustrates a block diagram of a layered prompt-based autonomous medical coding system to process clinical documents and encounter data through a multi-stage flow in accordance with one or more embodiments of the present disclosure.

Various detailed embodiments of the present disclosure, taken in conjunction with the accompanying FIGURES, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment", "in some embodiments", and "in at least some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

Typical solutions in the art are inadequate to address technical problems in computing architectures to (i) normalize heterogeneous clinical data sources into consistent, specialty-aware schemas, (ii) provide curated, provenance-tracked training corpora, and (iii) enable configuration-driven, continuous learning with rule-constrained validation to improve accuracy, robustness, and explainability in clinical documentation coding.

The present detailed description may provide illustrative embodiments of computer-based systems and methods for configuration-driven continuous training of large language models in autonomous medical coding. These embodiments may be described within the context of improving clinical documentation coding by addressing challenges such as inconsistent code selection across specialties, evolving payer and compliance requirements, and the limited availability of high-quality labeled datasets. The disclosed systems and methods may introduce mechanisms for normalizing heterogeneous clinical data into provenance-preserving, specialty-aware schemas, generating curated training corpora, and enabling continuous learning with rule-constrained validation to enhance accuracy, robustness, and explainability.

The embodiments described herein may be presented for illustrative purposes and may not be intended to impose limitations. Certain routine aspects related to computing components, network configurations, or commonly utilized algorithms may be omitted for clarity, as such aspects may be well-understood by those skilled in the art. The subject matter disclosed may not be confined to the specific arrangements or methodologies presented, and various modifications, substitutions, additions, and rearrangements may be implemented without departing from the spirit and scope defined by the claims. Examples provided herein may be intended to facilitate understanding and may not be meant to dictate a particular execution order or restrict selection among alternatives.

The terms used in this detailed description may be intended to be construed broadly to allow for variations in implementation. References to singular elements may include plural forms unless the context may clearly indicate otherwise. The term "based on" may allow for additional factors not explicitly described. The terms "and" and "or" may be used to describe alternatives and combinations of elements. Any reference to "in" may be understood to include "on" unless the context may specify otherwise. Examples and flow descriptions may be provided to aid understanding and may not be intended to require a particular execution order or exclusive selection among alternatives.

This detailed description may also include disclosures that describe components or functionalities that may be used in any combination with one another. Steps or operations may be performed in varying orders, may be omitted, or may be added without departing from the subject matter defined by the claims. Embodiments may include hardware, software, or combinations thereof. Software instructions may be stored on machine-readable media and may be executed by one or more processors to implement features described herein. References to specific technologies, standards, platforms, or code systems may be examples and may not limit the subject matter to those implementations. Publications cited throughout this document may be incorporated by reference in their entirety, and any such references may serve to further inform the understanding of the disclosed technology without limiting its scope.

In at least some embodiments, the disclosed technology may provide computer-implemented systems and methods that may enable configuration-driven continuous training of large language models in autonomous medical coding, where heterogeneous electronic health data and session-level event records may be normalized into a provenance-preserving, specialty-aware schema. In at least some embodiments, the schema may retain source lineage identifiers, version tags, and specialty metadata so downstream reasoning and validation stages may consume deterministically replayable context, and so operational outcomes may be traced back to the exact inputs, configurations, and evidence anchors used at the time of decision.

In at least some embodiments, the autonomous coding engine may implement a configurable, multi-stage reasoning pipeline that may sequentially determine evaluation and management levels, may infer procedure codes, may assign modifiers, may select diagnosis codes, and may link diagnoses to procedures, where each stage may be conditioned on prior stage outputs and may be guided by prompt templates and ranking parameters. In at least some embodiments, prompt templates may encode domain knowledge, payer policies, and documentation expectations, and ranking parameters may blend model scores, retrieval signals, and validation outcomes so the pipeline may produce candidate code bundles that may be both explainable and consistent across specialties.

In at least some embodiments, a rule-constrained validation and explainability layer may execute compiled policies that may include bundling rules, modifier applicability checks, and payer-specific compliance requirements, where the layer may generate machine-readable rationales that may include rule identifiers, evidence references to documentation spans, and pass or fail indicators.

In at least some embodiments, these validation artifacts may be persisted with provenance and versioning so downstream processes may audit decisions, may filter low-quality examples, and may mine constraints that may reinforce rule-consistent behavior during training and configuration updates. Stated differently, the system may store each validation artifact as a durable record together with metadata that traces its origin and history. The artifact may be saved along with:

- Source lineage: identifiers for the encounter, EHR system, document/note spans, and data sources used.
- Configuration versions: the exact model, prompt template, validation policy, and retrieval configuration versions active when the artifact was created.
- Timestamps and actors: when it was generated, by which service or user role (e.g., QA reviewer), and any subsequent edits or adjudications.
- Evidence anchors: references to the specific documentation spans or structured fields that support the validation decision.
- Integrity keys: hashes or IDs that allow deterministic replay of the pipeline against the same inputs/configuration.

Thus, by persisting the artifact with this provenance and versioning, downstream processes can audit how and why a decision was made, exclude low-quality or outdated examples, and extract rule-specific constraints to guide training and configuration updates.

In at least some embodiments, the user interface may be augmented with telemetry and event logging so interaction data associated with candidate or verified outputs may be captured, where the interaction data may include approvals, rejections, edits, rationales, timestamps, user roles, and model and prompt version identifiers.

In at least some embodiments, each interaction may be bound to the exact proposal and context snapshot reviewed, and may be persisted as part of an append-only lineage so a high-fidelity record may be available for adjudication, training example assembly, and deterministic replay.

In at least some embodiments, the system may generate provenance-tracked training examples by consolidating captured user interactions with validation results using a trust-weighted or quality-weighted consensus mechanism, where multiple inputs may be aggregated according to role-based weights, historical accuracy, and recency decay to select a single ground-truth outcome and a confidence score.

In at least some embodiments, the resulting training examples may include inputs such as schema-mapped context and evidence spans, may include outputs such as adjudicated labels and code linkages, and may include rationales such as rule identifiers and concise justification, all persisted with source lineage and configuration versions.

In at least some embodiments, a continuous learning engine may fuse signals from the reasoning pipeline, the validation checks, the captured user interactions, the provenance-tracked training examples, and/or downstream operational outcomes such as payer acceptances and denials, where the fused signals may be used to compute continuous learning indicators that may drive configuration updates.

In at least some embodiments, configuration data may include prompt templates, retrieval parameters, validation thresholds, and output ranking weights, and updates may be deployed through versioned rollout mechanisms that may include offline replay, shadow evaluation, and canary promotion without redeploying base models.

The technical problems addressed by this disclosure may relate to the translation of clinical documentation into standardized procedure and diagnosis codes for healthcare information systems. Conventional approaches may include manual review or static natural language processing models that may require periodic, large-scale retraining to adapt to specialty-specific documentation and evolving coding standards. These methods may be inefficient and may lack the ability to generalize across diverse clinical contexts. Retrieval techniques that may rely on keyword matching or rigid rules may fail to capture nuanced clinical context, which may result in inconsistent code selection. Additionally, the creation of high-quality labeled datasets for model training may be costly and slow, which may limit the frequency and effectiveness of model improvement cycles. Existing systems may not include integrated mechanisms to incorporate real-time feedback from users and automated validators, which may lead to model drift and reduced reliability. These limitations may highlight the need for a robust, scalable, and adaptive solution that may improve accuracy, consistency, and explainability in medical coding.

In at least some embodiments, the present disclosure may address these challenges by introducing computer-based systems and methods for configuration-driven continuous training of large language models in autonomous medical coding. The disclosed technical solutions may include a multi-layered architecture that may normalize heterogeneous clinical data sources into provenance-preserving, specialty-aware schemas. These schemas may include source lineage identifiers, version tags, and specialty metadata, which may enable deterministic replay and traceability of operational outcomes. A multi-stage reasoning pipeline may be implemented, where sequential language model layers may dynamically determine evaluation and management levels, may infer procedure codes, may assign modifiers, may predict diagnosis codes, and may establish linkages between diagnoses and procedures. Each stage may be conditioned on prior outputs and may be guided by domain-specific prompt templates and ranking parameters, which may ensure explainable and consistent code generation across specialties.

In at least some embodiments, the system may include a rule-constrained validation and explainability layer that may execute compiled policies, such as bundling rules, modifier applicability checks, and payer-specific compliance requirements. This layer may generate machine-readable rationales, which may include rule identifiers, evidence references, and pass/fail indicators, and may persist these with provenance and versioning for downstream auditing and training purposes. The system may also capture user interaction data, such as approvals, rejections, edits, and rationales, through an augmented user interface with telemetry and event logging. This interaction data may be consolidated with validation results using a trust-weighted adjudication mechanism to produce high-quality, provenance-tracked training examples. These examples may include schema-mapped context, adjudicated labels, and concise rationales, which may enable continuous learning and iterative updates to configuration data, such as prompt templates and ranking weights, without redeploying base models.

In at least some embodiments, the system may fuse signals from the reasoning pipeline, validation checks, user interactions, and downstream operational outcomes to facilitate adaptive configuration updates that may improve model accuracy, robustness, and compliance. The described system may transform routine operational activity into a disciplined, continuously improving training pipeline, which may address the limitations of conventional approaches and may enable scalable, explainable, and reliable autonomous medical coding.

FIG. 1 illustrates a block diagram of a layered prompt-based autonomous coding system 10 to process clinical documents and encounter data 20 through a multi-stage flow in accordance with one or more embodiments of the present disclosure. The system may integrate interconnected components so electronic health data may be transformed into explainable, validated coding outputs suitable for write-back into healthcare information systems.

In at least some embodiments, clinical documents and encounter data 20 may include structured record data and unstructured documentation text that may be routed to a pre-processor 25. The pre-processor 25 may perform context extraction and normalization so downstream stages may consume a schema-mapped context record with provenance and specialty-aware metadata.

In at least some embodiments, the schema-mapped context may be provided to LLM layers 30 implementing a multi-stage reasoning pipeline. The pipeline may sequentially execute E/M coding 35 to predict evaluation and management levels, Current Procedural Terminology (CPT) coding 40 to infer procedural codes conditioned on the E/M level and context, modifier logic 45 to determine applicable modifiers, diagnosis coding 50 to generate diagnosis codes, and diagnosis linking 55 to establish associations between diagnoses and procedures.

In at least some embodiments, a QA layer 60 may validate candidate outputs using ruleset-based verification and may generate machine-readable explanations. The QA layer 60 may verify internal consistency, apply bundling and payer-specific policies, and may emit verified outputs and validation rationale objects that may include rule identifiers, evidence references, and pass/fail indicators.

In at least some embodiments, EHR integration and write-back 65 may persist the validated results and associated rationale to clinical systems. The write-back 65 may update encounter records with the verified code bundle and may retain version tags so decisions may be deterministically replayed and audited against the exact context, pipeline configuration, and validation artifacts used at the time of coding.

Figure 2:
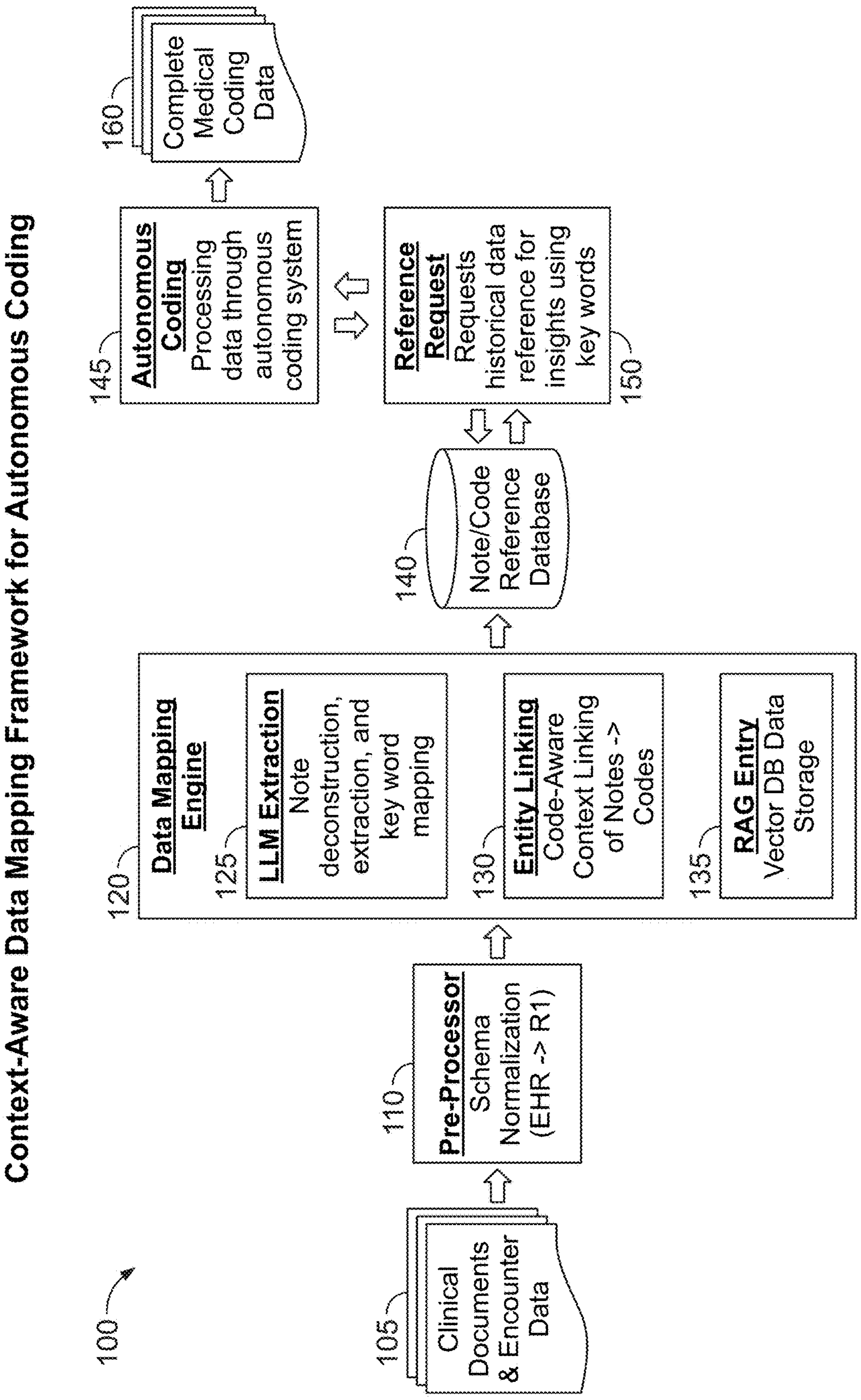
FIG. 2 is a block diagram of a context-aware data mapping framework to prepare clinical documents and encounter data for autonomous medical coding in accordance with one or more embodiments of the present disclosure.

FIG. 2 is a block diagram of a context-aware data mapping framework 100 to prepare clinical documents and encounter data 105 for autonomous coding in accordance with one or more embodiments of the present disclosure. The framework may orchestrate pre-processing, extraction, linking, and reference storage so downstream reasoning pipelines may consume a schema-normalized, provenance-preserving context enriched with specialty-aware metadata.

In at least some embodiments, a pre-processor 110 may normalize electronic health data from disparate sources into a common schema. The pre-processor 110 may standardize identifiers, timestamps, and code systems and may preserve source lineage so later stages may deterministically replay the exact inputs and configurations used during mapping.

In at least some embodiments, a data mapping engine 120 may include LLM extraction 125, entity linking 130, and RAG entry 135 modules. The LLM extraction 125 may perform note deconstruction, sectioning, span extraction, and keyword mapping to generate machine-readable documentation features. The entity linking 130 may perform code-aware context linking that may associate extracted spans and structured fields with candidate codes and modifiers, retaining evidence anchors and rationale snippets. The RAG entry 135 may persist mapped exemplars and embeddings into a vector database so similar note/code cases may be retrieved on demand.

In at least some embodiments, a note/code reference database 140 may store normalized exemplars with provenance and specialty metadata. The database 140 may index documentation spans, code assignments, and linkage information so retrieval may surface high-relevance examples for enrichment of downstream reasoning and validation.

In at least some embodiments, autonomous coding 145 may consume schema-mapped context and may optionally issue a reference request 150 to the note/code reference database 140. The reference request 150 may retrieve related exemplars using keywords or embeddings so the autonomous coder 145 may incorporate evidence-anchored context while generating candidate outputs and explanations.

In at least some embodiments, the context-aware data mapping framework may yield complete medical coding data 160 after the autonomous coder 145 processes the mapped context and retrieved exemplars. The resulting outputs may include verified code bundles, diagnosis-to-procedure linkages, and validation rationale objects that may be persisted with provenance so operational outcomes may be audited and replayed.

Figure 3:
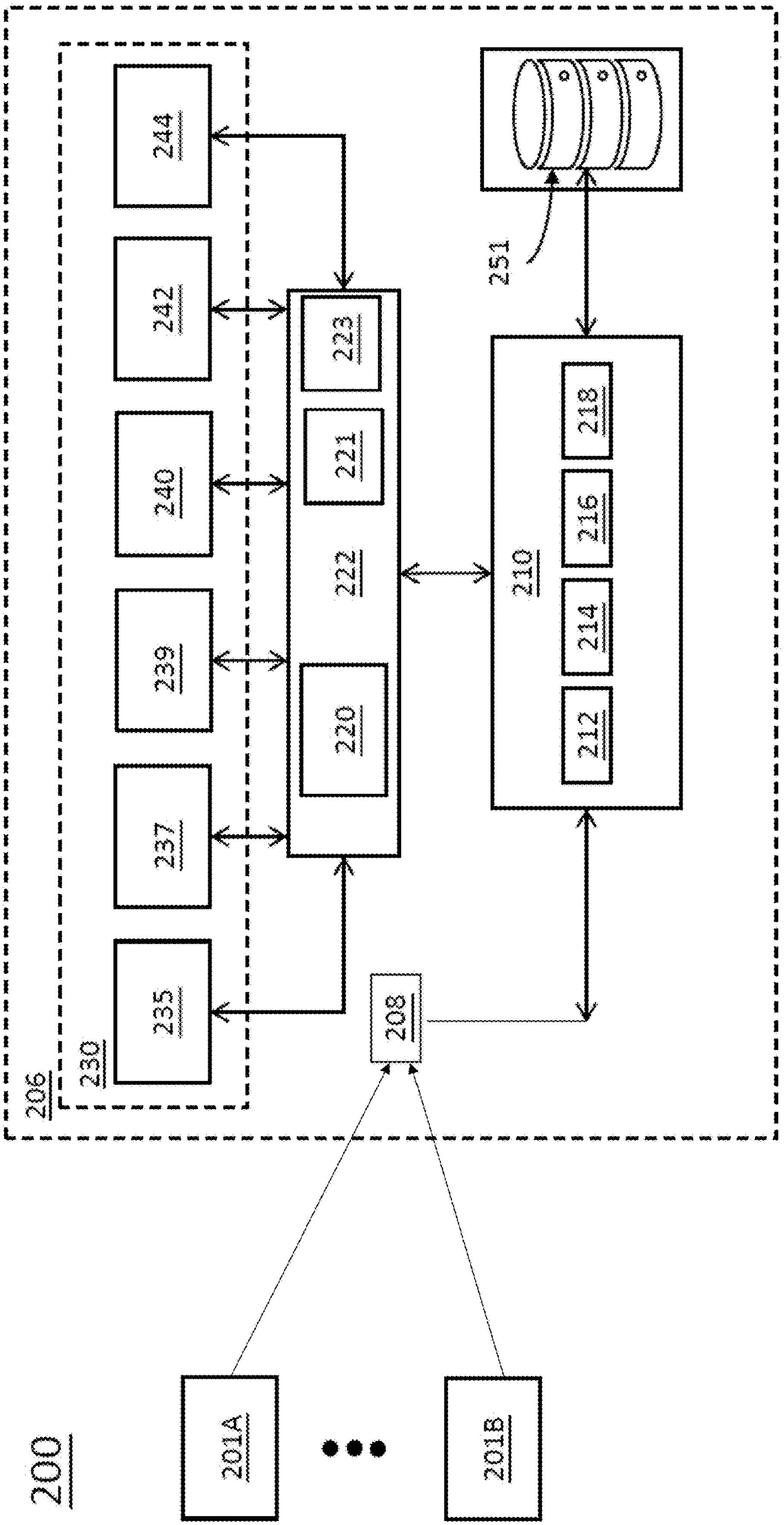
FIG. 3 is a block diagram of a system for implementing configuration-driven continuous training and autonomous medical coding based on an autonomous medical coding and continuous learning microservices platform in accordance with one or more embodiments of the present disclosure.

FIG. 3 is a block diagram of a system 200 for implementing configuration-driven continuous training and autonomous medical coding based on an autonomous medical coding and continuous learning (AMCCL) microservices platform 206 in accordance with one or more embodiments of the present disclosure. Aspects of the present disclosure may be applied to any embodiment for the microservices platform 206 that may include software modules denoted 235, 237, 239, 240 and 244 for implementing the AMCCL microservices in a service layer 230 as described hereinbelow. The software modules 235, 237, 239, 240 and 244 may be for example, the ingestion and connectivity service, the normalization and provenance service, the context mapping and retrieval service, the reasoning pipeline orchestrator, and the validation and adjudication/training example service.

In at least some embodiments, the AMCCL microservices platform 206 may include a multi-layered architecture including, for example, the service layer 230, an orchestration layer 222, and a platform layer 210, however other layers may be additionally contemplated. In at least some embodiments, a plurality of N electronic resources denoted 201A . . . 201B may interact with the AMCCL microservices platform 206, where N may be an integer. Communications from the plurality of electronic resources 201A . . . 201B may be received by a communication circuitry 208 and may then be routed to an appropriate component of the system, via the platform layer 210, for example.

In at least some embodiments, the platform layer 210 may include an input/output (I/O) interface 212 for facilitating data communication to external devices, such as, e.g., the communication circuitry 208 with any other system devices. The platform layer 210 may also include a runtime environment 214 for implementing programs, services, functionalities and microservices using a plurality of processors 216 and memory devices 218 in a plurality of computing machines such as the M computing machines for implementing the AMCCL microservices platform 206. The memory devices 218 may include, e.g., temporary storage and caching of data to facilitate resources of the AMCCL microservices platform 206.

In at least some embodiments, the platform layer 210 includes functionality for, e.g., secure configuration distribution, versioned rollout and canary promotion, telemetry collection, logging and tracing, and policy enforcement, as well as any other functions pertaining to platform level functionality.

In at least some embodiments, the orchestrator 220 may manage operations of the AMCCL microservices platform 206, including allocation of resources (e.g., add or removing any number of the computing machines) by a load balancer 223, process schedule with, e.g., the plurality of processors 216, among other tasks. For example, in at least some embodiments, the orchestrator 220 may include a plurality of application programming interfaces (APIs) 221 for calling services and functions of the AMCCL microservices platform 206 in interacting with the plurality of electronic resources 201A . . . 201B.

In at least some embodiments, the orchestrator 220 may manage operations of microservices in a service layer 230 and coordination of the service layer 230 with the platform layer 210. For example, the service layer 230 may include software modules 235, 237, 239, 240 and 244 related to, for example, implementing the AMCCL microservices platform for configuration-driven continuous training and autonomous medical coding. In at least some embodiments, the orchestrator 220 may facilitate aggregation of data from multiple domains in the service layer 230 and/or may orchestrate data-related operations across domains and services to provide for complete experiences within any given domain.

In at least some embodiments, the database 251 as described above may be separate from databases stored in the plurality of memories stored in the plurality of computing machines.

In at least some embodiments, any data stored the plurality of databases may be accessible from the plurality of N electronic resources 201A . . . 201B via any of the plurality of APIs 221 in the orchestration layer 222 in the AMCCL microservices platform 606.

In at least some embodiments, the AMCCL microservices platform 206 may ingest clinical documents and encounter data from electronic resources 201A . . . 201B so the ingestion and connectivity service (module 235) may route inputs to the pre-processor 25 of FIG. 1 and the pre-processor 110 of FIG. 2, where the communication circuitry 208 and I/O interface 212 may facilitate authenticated transfer of structured record data, unstructured documentation text, and session-level event records into the platform layer 210.

In at least some embodiments, the normalization and provenance service (module 237) may operate in the runtime environment 214 across processors 216 and memory devices 218 so electronic health data may be normalized into the provenance-preserving, specialty-aware schema described for FIGS. 1 and 2, where source lineage identifiers, timestamps, and configuration version tags may be persisted in database 251 to enable deterministic replay of the LLM layers 30 and the data mapping engine 120.

In at least some embodiments, the context mapping and retrieval service (module 239) may implement the data mapping engine 120 of FIG. 2 so LLM extraction 125 may perform note deconstruction and span extraction, entity linking 130 may associate evidence anchors to candidate codes and modifiers, and RAG entry 135 may persist embeddings and mapped exemplars into the note/code reference database 140, where the autonomous coder 145 may issue a reference request 150 to retrieve similar cases.

In at least some embodiments, the reasoning pipeline orchestrator (module 240) may coordinate LLM layers 30 in FIG. 1 so E/M coding 35 may run prior to CPT coding 40, modifier logic 45 may adjust applicable modifiers, diagnosis coding 50 may generate diagnosis codes, and diagnosis linking 55 may establish diagnosis-to-procedure associations, where prompt templates and output ranking parameters may be distributed by the platform layer 210 using secure configuration distribution and versioned rollout.

In at least some embodiments, the validation and adjudication/training example service (module 244) may implement the QA layer 60 of FIG. 1 so ruleset-based verification may execute bundling rules, modifier applicability checks, and payer policies, where validation rationale objects may include rule identifiers, evidence references, and pass/fail indicators, and where telemetry-captured user interaction data from the user interface may be consolidated into provenance-tracked training examples using trust- or quality-weighted consensus.

In at least some embodiments, the orchestration layer 222 and orchestrator 220 may manage service layer 230 operations so the load balancer 223 may allocate compute for high-throughput LLM stages and retrieval workloads, APIs 221 may expose calls to the pre-processor 25, LLM layers 30, data mapping engine 120, QA layer 60, and EHR integration and write-back 65, and tracing/logging may record event flows linking FIGS. 1 and 2 components to the microservices platform 206.

In at least some embodiments, database 251 may persist schema-mapped context records from FIGS. 1 and 2, note-to-code linkage graphs, validation rationale objects, user interaction telemetry, and generated provenance-tracked training examples, where versioned labels and context hashes may enable deterministic replay of E/M coding 35 through diagnosis linking 55 and reproducible retrieval via the note/code reference database 140.

In at least some embodiments, the platform layer 210 may provide secure configuration distribution, canary promotion, and shadow evaluation so updated prompt templates, retrieval parameters, validation thresholds, and output ranking weights may be rolled out to LLM layers 30 and the QA layer 60, where offline replay against stored schema-mapped context and validation artifacts may gate promotion to production.

In at least some embodiments, EHR integration and write-back 65 from FIG. 1 may be implemented as an API 221 in the service layer 230 so verified outputs and associated rationale objects may be written to external clinical systems, where version tags and provenance may be stored in database 251 and exposed for audit and adjudication workflows coordinated by module 244.

Figure 4:
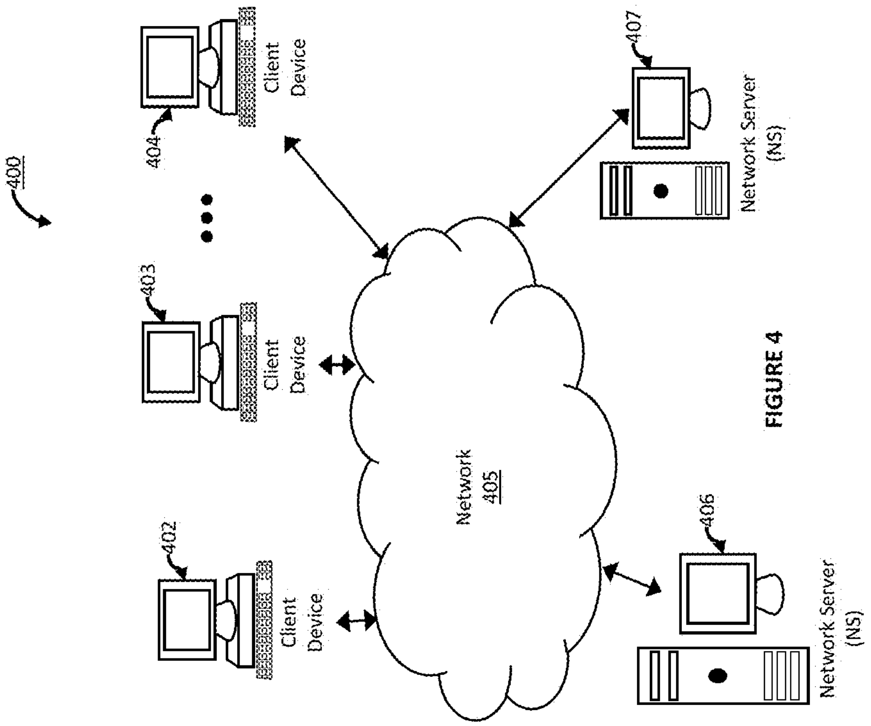
FIG. 4 depicts a block diagram of a computer-based system/platform in accordance with one or more embodiments of the present disclosure.

FIG. 4 depicts a block diagram of an exemplary computer-based system/platform 400 in accordance with one or more embodiments of the present disclosure. However, not all of these components may be required to practice one or more embodiments, and variations in the arrangement and type of the components may be made without departing from the spirit or scope of various embodiments of the present disclosure. In at least some embodiments, the exemplary inventive computing devices and/or the exemplary inventive computing components of the exemplary computer-based system/platform 400 may be configured to implement configuration-driven continuous training and autonomous medical coding using provenance-preserving normalization, multi-stage reasoning pipelines, ruleset-based validation with machine-readable explanations, telemetry-enabled user interaction capture, and generation of provenance-tracked training examples for iterative configuration updates, as detailed herein. In at least some embodiments, the exemplary computer-based system/platform 400 may be based on a scalable computer and/or network architecture that incorporates varies strategies for assessing the data, caching, searching, and/or database connection pooling. An example of the scalable architecture is an architecture that is capable of operating multiple servers.

In at least some embodiments, referring to FIG. 4, source devices 402-404 (e.g., client devices) of the exemplary computer-based system/platform 400 may include virtually any computing device capable of receiving and sending a message over a network (e.g., cloud network), such as network 405, to and from another computing device, such as servers 406 and 407, each other, and the like. Here, source devices 402-404 may be the plurality of N source data devices 305A . . . 305N. In at least some embodiments, the source devices 402-404 may be personal computers, multiprocessor systems, microprocessor-based or programmable consumer electronics, network PCs, and the like.

In at least some embodiments, one or more source devices within source devices 402-404 may include computing devices that typically connect using a wireless communications medium such as vehicles, vehicle sensors, cell phones, smart phones, pagers, walkie talkies, radio frequency (RF) devices, infrared (IR) devices, CBs, integrated devices combining one or more of the preceding devices, or virtually any mobile computing device, and the like. In at least some embodiments, one or more source devices within source devices 402-404 may be devices that are capable of connecting using a wired or wireless communication medium such as a PDA, POCKET PC, wearable computer, a laptop, tablet, desktop computer, a netbook, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, satellite, ZigBee, etc.). In at least some embodiments, one or more source devices within source devices 402-404 may include may run one or more applications, such as Internet browsers, mobile applications, voice calls, videoconferencing, and email, among others. In at least some embodiments, one or more source devices within source devices 402-404 may be configured to receive and to send data such as clinical documentation, billing records, laboratory results, imaging reports, telemetry event logs, configuration updates, validation artifacts, and user interaction data, and the like.

In at least some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In at least some embodiments, a source device within source devices 402-404 may be specifically programmed by either Java, .Net, QT, C, C++ and/or other suitable programming language.

In at least some embodiments, the exemplary network 405 may provide network access, data transport and/or other services to any computing device coupled to it. In at least some embodiments, the exemplary network 405 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In at least some embodiments, the exemplary network 405 may implement one or more of a GSM architecture, a General Packet Radio Service (GPRS) architecture, a Universal Mobile Telecommunications System (UMTS) architecture, and an evolution of UMTS referred to as Long Term Evolution (LTE).

In at least some embodiments and, optionally, in combination of any embodiment described above or below, the exemplary network 405 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In at least some embodiments and, optionally, in combination of any embodiment described above or below, at least one computer network communication over the exemplary network 405 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, satellite and any combination thereof.

In at least some embodiments, the exemplary network 405 may also include mass storage, such as network attached storage (NAS), a storage area network (SAN), a content delivery network (CDN) or other forms of computer or machine readable media.

In at least some embodiments, the exemplary server 406 or the exemplary server 407 may be a web server (or a series of servers) running a network operating system, examples of which may include but are not limited to Microsoft Windows Server, Novell NetWare, or Linux. In at least some embodiments, the exemplary server 406 or the exemplary server 407 may be used for and/or provide cloud and/or network computing.

In at least some embodiments, one or more of the exemplary servers 406 and 407 may be specifically programmed to perform, in non-limiting example, as authentication servers, search servers, email servers, social networking services servers, SMS servers, IM servers, MMS servers, exchange servers, health care-related services servers, or any similarly suitable service-base servers for users of the source devices 402-404.

In at least some embodiments and, optionally, in combination of any embodiment described above or below, for example, one or more exemplary source devices 402-404, the exemplary server 406, and/or the exemplary server 407 may include a specifically programmed software module that may be configured to send, process, and receive information using a scripting language, a remote procedure call, an email, a tweet, Short Message Service (SMS), Multimedia Message Service (MMS), instant messaging (IM), internet relay chat (IRC), mIRC, Jabber, an application programming interface, Simple Object Access Protocol (SOAP) methods, Common Object Request Broker Architecture (CORBA), HTTP (Hypertext Transfer Protocol), REST (Representational State Transfer), or any combination thereof.

Figure 5:
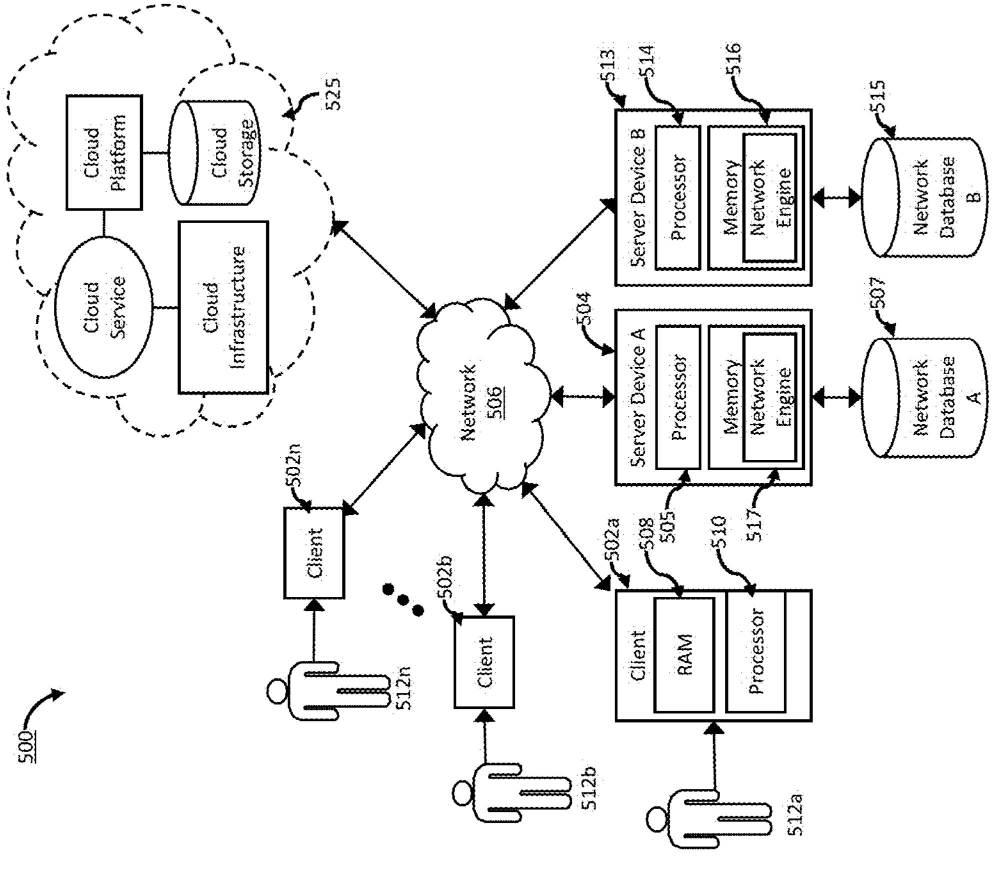
FIG. 5 depicts a block diagram of another computer-based system/platform in accordance with one or more embodiments of the present disclosure.

FIG. 5 depicts a block diagram of another exemplary computer-based system/platform 500 in accordance with one or more embodiments of the present disclosure. However, not all of these components may be required to practice one or more embodiments, and variations in the arrangement and type of the components may be made without departing from the spirit or scope of various embodiments of the present disclosure. In at least some embodiments, the source computing devices 502*a*, 502*b* thru 502*n* shown each at least includes a computer-readable medium, such as a random-access memory (RAM) 508 coupled to a processor 510 or FLASH memory. Here, source (e.g., client) devices 502*a*, 502*b* thru 502*n* may be the plurality of N source data devices 305A . . . 305N.

In at least some embodiments, the processor 510 may execute computer-executable program instructions stored in memory 508. In at least some embodiments, the processor 510 may include a microprocessor, an ASIC, and/or a state machine. In at least some embodiments, the processor 510 may include, or may be in communication with, media, for example computer-readable media, which stores instructions that, when executed by the processor 510, may cause the processor 510 to perform one or more steps described herein. In at least some embodiments, examples of computer-readable media may include, but are not limited to, an electronic, optical, magnetic, or other storage or transmission device capable of providing a processor, such as the processor 510 of client 502*a*, with computer-readable instructions. In at least some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In at least some embodiments, the instructions may comprise code from any computer-programming language, including, for example, C, C++, Visual Basic, Java, Python, Perl, JavaScript, and etc.

In at least some embodiments, source computing devices 502*a* through 502*n* may also comprise a number of external or internal devices such as a mouse, a CD-ROM, DVD, a physical or virtual keyboard, a display, a speaker, or other input or output devices. In at least some embodiments, examples of source computing devices 502*a* through 502*n* (e.g., clients) may be any type of processor-based platforms that are connected to a network 506 such as, without limitation, personal computers, digital assistants, personal digital assistants, smart phones, pagers, digital tablets, laptop computers, Internet appliances, and other processor-based devices.

In at least some embodiments, source computing devices 502*a* through 502*n* may be specifically programmed with one or more application programs in accordance with one or more principles/methodologies detailed herein. In at least some embodiments, source computing devices 502*a* through 502*n* may operate on any operating system capable of supporting a browser or browser-enabled application, such as Microsoft™, Windows™, and/or Linux. In at least some embodiments, source computing devices 502*a* through 502*n* shown may include, for example, personal computers executing a browser application program such as Microsoft Corporation's Internet Explorer™, Apple Computer, Inc.'s Safari™, Mozilla Firefox, and/or Opera. In at least some embodiments, through the source computing client devices 502*a* through 502*n*, may communicate over the exemplary network 506 with each other and/or with other systems and/or devices coupled to the network 506. As shown in FIG. 5, exemplary server devices 504 and 513 may be also coupled to the network 506. In at least some embodiments, one or more source computing devices 502*a* through 502*n* may be mobile clients.

In at least some embodiments, at least one database of exemplary databases 507 and 515 may be any type of database, such as the database 362 described above, including a database managed by a database management system (DBMS). In at least some embodiments, an exemplary DBMS-managed database may be specifically programmed as an engine that controls organization, storage, management, and/or retrieval of data in the respective database. In at least some embodiments, the exemplary DBMS-managed database may be specifically programmed to provide the ability to query, backup and replicate, enforce rules, provide security, compute, perform change and access logging, and/or automate optimization. In at least some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In at least some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In at least some embodiments, the exemplary DBMS-managed database may be specifically programmed to include metadata about the data that is stored.

Figure 6:
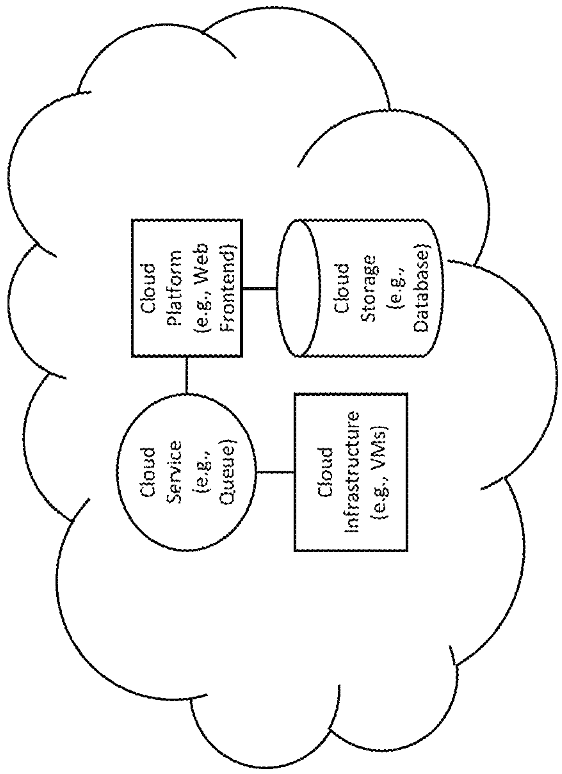
FIG. 6 depicts a block diagram of another computer-based system/platform in accordance with one or more embodiments of the present disclosure.
Figure 7:
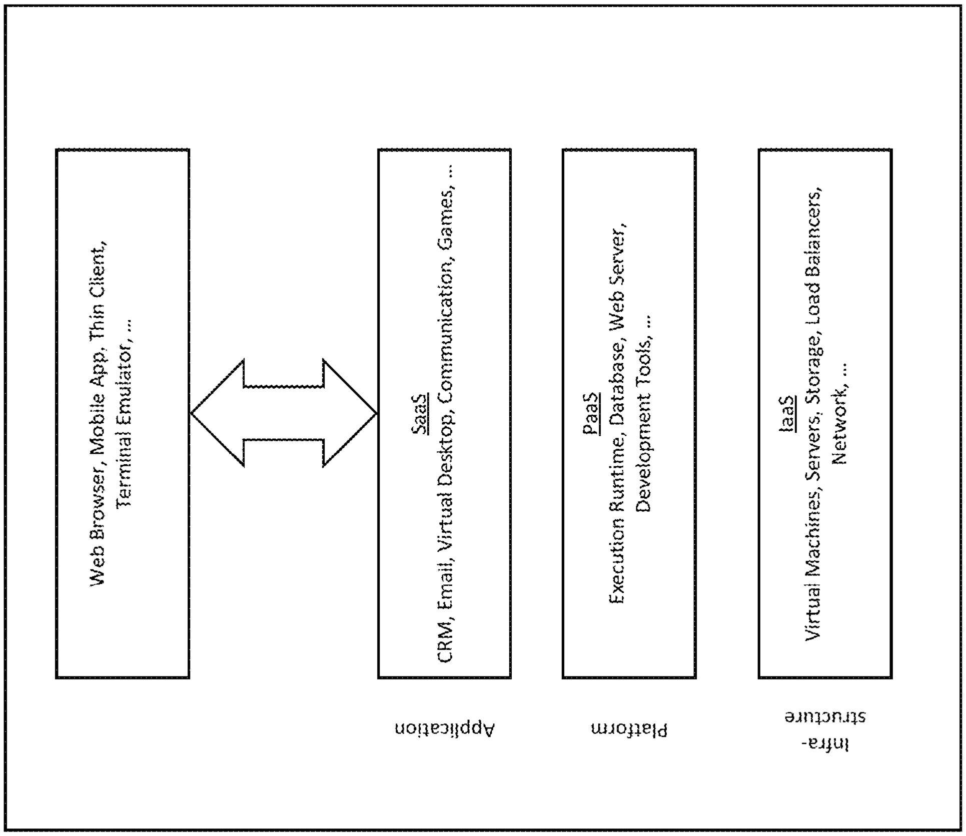
FIG. 7 illustrates schematics of implementations of the cloud computing/architecture(s) in which embodiments of a system for configuration-driven continuous training of large language models in autonomous coding may be specifically configured to operate in accordance with some embodiments of the present disclosure.

In at least some embodiments, the exemplary inventive computer-based systems/platforms, the exemplary inventive computer-based devices, and/or the exemplary inventive computer-based components of the present disclosure may be specifically configured to operate in a cloud computing/architecture such as, but not limiting to: infrastructure a service (IaaS), platform as a service (PaaS), and/or software as a service (SaaS). FIGS. 6 and 7 illustrate schematics of exemplary implementations of the cloud computing/architecture(s) in which the exemplary inventive computer-based systems/platforms, the exemplary inventive computer-based devices, and/or the exemplary inventive computer-based components of the present disclosure may be specifically configured to operate.

The aforementioned examples are, of course, illustrative and not restrictive.

In at least some embodiments, a trust-weighted adjudication mechanism may aggregate inputs from coder interactions captured via the user interface exposed by APIs 221 of the orchestration layer 222 and module 244 of FIG. 3, where decisions reviewed against validation rationale objects emitted by the QA layer 60 of FIG. 1 may be consolidated to select a ground-truth outcome. In at least some embodiments, the consensus decision y*may be selected using a weighted vote defined as $$y^* = \underset{y \in Y}{\operatorname{argmax}} \sum_i w_i \cdot 1[y_i = y]$$

where expert auditors operating through module 244 may short-circuit consensus for definitive resolutions.

In at least some embodiments, a trust weight model may include role-dependent scaling, reviewer accuracy, and recency decay so recent, reliable inputs may be emphasized across the adjudication/training example service 244 of FIG. 3, where the composite weight may be expressed as $$w_i = \alpha_{role(i)} \cdot \gamma_{accuracy(i)} \cdot e^{-\lambda \cdot \Delta t_i}$$

and tiered overrides may allow expert decisions to prevail when consensus margins may be low.

In at least some embodiments, confidence scores may be assigned to adjudicated labels produced by module 244 and persisted in database 251 of FIG. 3 so downstream training procedures may weight examples according to label reliability, where a confidence-weighted loss may be applied during optimization as $$L = \sum_j w_j \cdot \ell(\hat{y}^j, y_j^*)$$

and higher confidence examples may be prioritized during continuous learning coordinated by the platform layer 210.

In at least some embodiments, a cross-application data fusion engine may merge signals originating from the layered prompt-based autonomous coding system 10 of FIG. 1, the QA layer 60 of FIG. 1, and downstream EHR write-back 65 of FIG. 1 together with payer outcomes accessible to the service layer 230 of FIG. 3, where events may be keyed by encounter identifiers and code candidate identifiers and may retain lineage to model, prompt, and validation versions distributed by the platform layer 210.

In at least some embodiments, a fusion scoring function may be calculated within module 244 to quantify decision strength for configuration updates across the reasoning pipeline orchestrator 240 of FIG. 3, where the score s may be derived from multiple operational signals as:

$$s = \beta_1 \cdot \text{QA\_pass} + \beta_2 \cdot \text{validation\_pass} + \beta_3 \cdot \text{payment\_success} - \beta_4 \cdot \text{denial} - \beta_5 \cdot \text{edit\_reversal}$$

and thresholds may be calibrated per specialty and payer using telemetry stored in database 251.

In at least some embodiments, configuration-driven prompt and ranking updates may be triggered by fused signals and distributed by secure configuration mechanisms of the platform layer 210 in FIG. 3 so prompt templates for E/M coding 35, CPT coding 40, modifier logic 45, diagnosis coding 50, and diagnosis linking 55 of FIG. 1 may be refined without redeploying base models, where updates may be gated by offline replay, shadow evaluation, and canary promotion controlled by the orchestrator 220 and load balancer 223.

In at least some embodiments, a rule-constrained validation and explainability layer corresponding to QA layer 60 of FIG. 1 and validation logic in module 244 of FIG. 3 may perform structured clinical checks so modifier validity, bundling logic, and documentation sufficiency may be enforced prior to EHR write-back 65, where machine-readable explanations may include rule identifiers and evidence references to documentation spans derived from the data mapping engine 120 of FIG. 2.

In at least some embodiments, validation and explainability outputs emitted by QA layer 60 may be mined within module 244 into training constraints and weak supervision features so rule-specific expectations may be reinforced across LLM layers 30 of FIG. 1, where failures may generate negative examples or penalty signals and successful justifications may provide features such as expected rule citations for specific code families.

In at least some embodiments, a context-aware data mapping framework may include LLM-assisted extraction 125 and entity linking 130 within the data mapping engine 120 of FIG. 2 so note deconstruction, sectioning, span extraction, negation and uncertainty detection, and temporal cue identification may be performed, where extracted features may be normalized by the pre-processor 110 into a specialty-aware schema with provenance preserved in database 251 of FIG. 3.

In at least some embodiments, code-aware entity linking 130 may associate documentation spans and structured fields to candidate CPT, HCPCS, ICD, and modifier codes used by the reasoning stages 35, 40, 45, and 50 of FIG. 1, where links may include confidence values, rationale snippets, specialty tags, and payer context so training pairs may capture precise note-to-code alignments anchored in clinical evidence stored in the note/code reference database 140 of FIG. 2.

In at least some embodiments, diagnosis-to-procedure and modifier linking may be encoded as a directed graph produced during diagnosis linking 55 of FIG. 1 and maintained by database 251 of FIG. 3 so allowable associations, typical sequencing, and payer-specific exceptions may be captured, where links may be emitted with certainty and provenance so multi-label outputs may be trained with linkage constraints by the reasoning pipeline orchestrator 240.

In at least some embodiments, QA layer outputs 60 may be treated as curated labels by module 244 so verified decisions, disagreements, and reconciliations may be recorded as structured artifacts with versioning and reviewer identity, where only high-confidence, rule-consistent outcomes may be promoted into a "golden" training set accessible to the context mapping and retrieval service 239.

In at least some embodiments, a note/code reference database 140 of FIG. 2 may store mapped historical exemplars and embeddings generated by RAG entry 135 with specialty and payer metadata so retrieval by autonomous coding 145 may enrich training batches with high-relevance examples, where hard negatives may be generated from near-miss cases rejected by QA layer 60 or denied by payers and persisted in database 251.

In at least some embodiments, retrieval policies executed by the context mapping and retrieval service 239 of FIG. 3 may prioritize recency and specialty matching so evolving payer behavior and documentation styles may be reflected in training enrichment, where rare specialties and edge cases may be up-weighted to improve recall on low-frequency patterns across LLM layers 30 of FIG. 1.

In at least some embodiments, sample weighting, curriculum learning, and drift management may be applied by the continuous learning engine operating within module 240 and module 244 of FIG. 3 so training may begin with high-confidence "golden" examples from database 251, may progressively introduce harder cases including prior denials later overturned, and may monitor shifts in payer denials and QA disagreement rates to trigger targeted data collection and prompt tuning per specialty and payer.

In at least some embodiments, deterministic replay procedures may be implemented across the pre-processor 25 of FIG. 1, the data mapping engine 120 of FIG. 2, and the reasoning pipeline orchestrator 240 of FIG. 3 so context snapshot hashes and version tags for models, prompts, validation policies, and retrieval configurations may be captured in database 251, where the pipeline may be re-executed against the exact stored inputs and configurations to reproduce decisions for audit and regression evaluation.

In at least some embodiments, telemetry instrumentation in the user interface exposed via APIs 221 may capture approvals, rejections, edits, rationales, timestamps, user role identifiers, and model, prompt, and validation version identifiers for candidate outputs generated by LLM layers 30 and validated by QA layer 60 of FIG. 1, where each interaction may be bound to the exact proposal and context snapshot reviewed and may be persisted in an append-only lineage for adjudication and training assembly in module 244.

In at least some embodiments, a feature store hosted in database 251 and managed by the service layer 230 may maintain unified events keyed by (encounter_id, code_candidate_id) with lineage to configuration versions and context hashes produced by pre-processor 110 of FIG. 2, where reproducible retrieval by the note/code reference database 140 and fine-grained analysis of operational outcomes may be enabled for continuous learning.

In at least some embodiments, acceptance thresholds and ranking weights in the reasoning pipeline stages 35, 40, 45, 50, and 55 of FIG. 1 may be adapted using continuous learning indicators computed by module 244 and orchestrated by module 240 of FIG. 3, where specialty-specific calibration and payer-specific calibration may be performed to reduce denial rates and improve reimbursement consistency while maintaining explainability and compliance across QA layer 60 and EHR integration and write-back 65.

Figure 8:
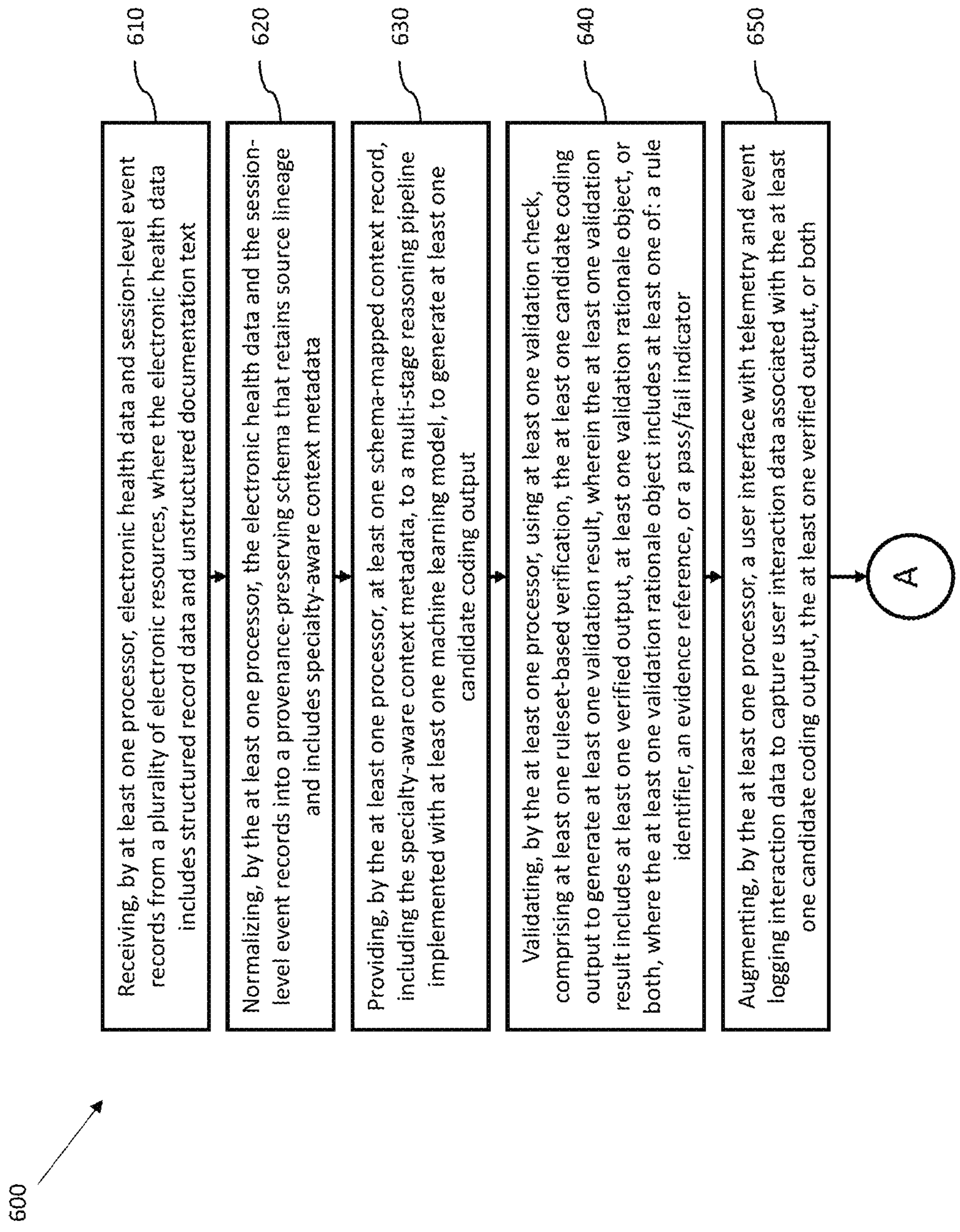
FIG. 8 is a flowchart of a method for configuration-driven continuous training of large language models in autonomous medical coding in accordance with one or more embodiments of the present disclosure.
Figure 8:
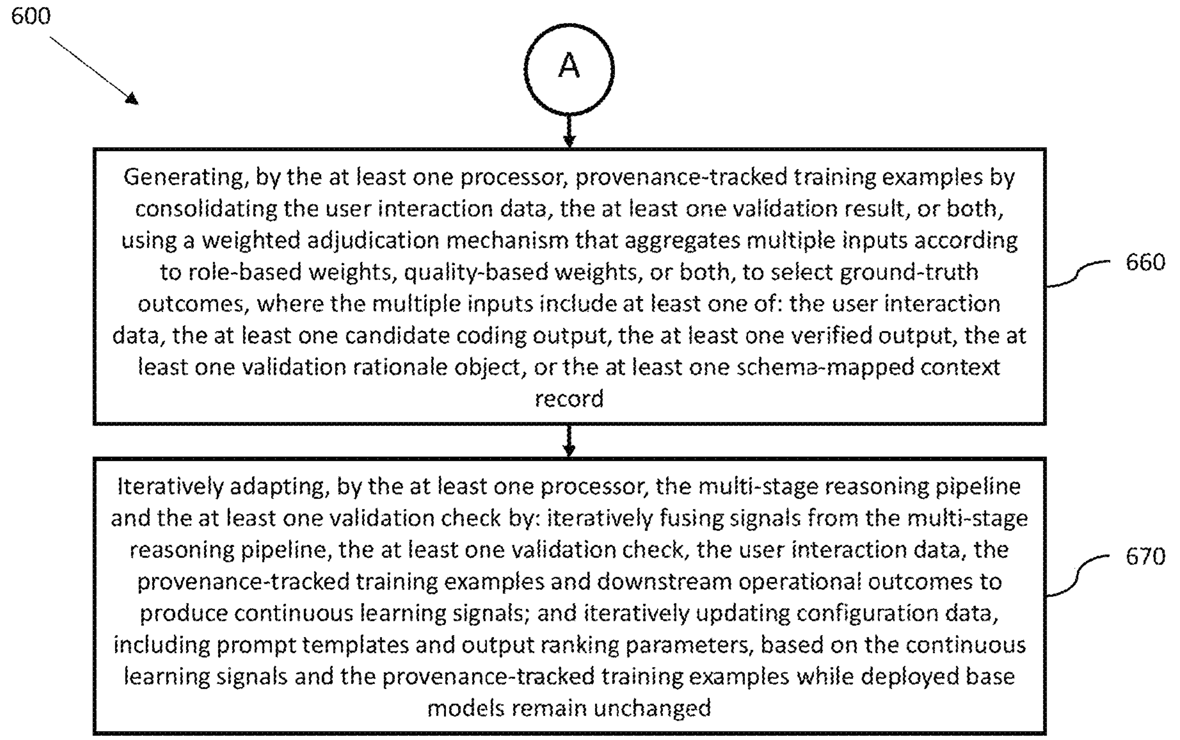

FIG. 8 is a flowchart of an exemplary method 600 for configuration-driven continuous training of large language models in autonomous medical coding in accordance with one or more embodiments of the present disclosure. The method may be performed by any of the plurality of processors 216 of FIG. 3, for example.

In at least some embodiments, the method 600 may include receiving 610, by at least one processor, electronic health data and session-level event records from a plurality of electronic resources, where the electronic health data includes structured record data and unstructured documentation text.

In at least some embodiments, the method 600 may include normalizing 620, by the at least one processor, the electronic health data and the session-level event records into a provenance-preserving schema that retains source lineage and includes specialty-aware context metadata.

In at least some embodiments, the method 600 may include providing 630, by the at least one processor, at least one schema-mapped context record, including the specialty-aware context metadata, to a multi-stage reasoning pipeline implemented with at least one machine learning model, to generate at least one candidate coding output.

In at least some embodiments, the method 600 may include validating 640, by the at least one processor, using at least one validation check, including at least one ruleset-based verification, the at least one candidate coding output to generate at least one validation result, where the at least one validation result includes at least one verified output, at least one validation rationale object, or both, where the at least one validation rationale object includes at least one of: a rule identifier, an evidence reference, or a pass/fail indicator.

In at least some embodiments, the method 600 may include augmenting 650, by the at least one processor, a user interface with telemetry and event logging interaction data to capture user interaction data associated with the at least one candidate coding output, the at least one verified output, or both.

In at least some embodiments, the method 600 may include generating 660, by the at least one processor, provenance-tracked training examples by consolidating the user interaction data, the at least one validation result, or both, using a weighted adjudication mechanism that aggregates multiple inputs according to role-based weights, quality-based weights, or both, to select ground-truth outcomes, where the multiple inputs include at least one of: the user interaction data, the at least one candidate coding output, the at least one verified output, the at least one validation rationale object, or the at least one schema-mapped context record.

In at least some embodiments, the method 600 may include iteratively adapting 670, by the at least one processor, the multi-stage reasoning pipeline and the at least one validation check by: iteratively fusing signals from the multi-stage reasoning pipeline, the at least one validation check, the user interaction data, the provenance-tracked training examples and downstream operational outcomes to produce continuous learning signals; and iteratively updating configuration data, including prompt templates and output ranking parameters, based on the continuous learning signals and the provenance-tracked training examples while deployed base models remain unchanged.

In at least some embodiments, the system may iteratively update configuration data that may include prompt templates and output ranking parameters based on continuous learning signals and provenance-tracked training examples, where continuous learning signals may be computed by fusing outcomes from the multi-stage reasoning pipeline, rule-constrained validation checks, telemetry-captured user interactions, and downstream operational indicators such as payer acceptances and denials, and where provenance-tracked training examples may encode schema-mapped context, adjudicated labels, evidence anchors, rationales, confidence scores, and versioned lineage to inputs and configurations.

In at least some embodiments, prompt templates may be refined to incorporate specialty-aware guidance, payer policy inserts, documentation expectations, and retrieval hints, and output ranking parameters may be adjusted to rebalance candidate selection using blended scores derived from model outputs, retrieval relevance, validation pass/fail results, and historical payment performance.

In at least some embodiments, these configuration-driven updates may be orchestrated through a versioned rollout that may include offline replay against stored context snapshots, shadow evaluation against live traffic, and canary promotion gated by pre-defined acceptance thresholds, where audit trails record configuration versions, context hashes, and decision artifacts to enable deterministic replay and roll-back.

In at least some embodiments, the updates may be applied while the deployed base models remain unchanged, where the base models may refer to the underlying pretrained or foundation model artifacts and their weights used by the reasoning pipeline, and the adaptive behavior may be achieved by modifying only the surrounding configuration controls rather than retraining, replacing, or redeploying those base model artifacts.

In at least some embodiments, a computer-implemented method may include receiving, by at least one processor, electronic health data and session-level event records from a plurality of electronic resources, where the electronic health data may include structured record data and unstructured documentation text; normalizing, by the at least one processor, the electronic health data and the session-level event records into a provenance-preserving schema that may retain source lineage and may include specialty-aware context metadata; providing, by the at least one processor, at least one schema-mapped context record, including the specialty-aware context metadata, to a multi-stage reasoning pipeline implemented with at least one machine learning model, to generate at least one candidate coding output; validating, by the at least one processor, using at least one validation check, including at least one ruleset-based verification, the at least one candidate coding output to generate at least one validation result; where the at least one validation result may include at least one verified output, at least one validation rationale object, or both; where the at least one validation rationale object may include at least one of: a rule identifier, an evidence reference, or a pass/fail indicator; augmenting, by the at least one processor, a user interface with telemetry and event logging interaction data to capture user interaction data associated with the at least one candidate coding output, the at least one verified output, or both; generating, by the at least one processor, provenance-tracked training examples by consolidating the user interaction data, the at least one validation result, or both, using a weighted adjudication mechanism that may aggregate multiple inputs according to role-based weights, quality-based weights, or both, to select ground-truth outcomes; where the multiple inputs may include at least one of: the user interaction data, the at least one candidate coding output, the at least one verified output, the at least one validation rationale object, or the at least one schema-mapped context record; and iteratively adapting, by the at least one processor, the multi-stage reasoning pipeline and the at least one validation check by iteratively fusing signals from the multi-stage reasoning pipeline, the at least one validation check, the user interaction data, the provenance-tracked training examples and downstream operational outcomes to produce continuous learning signals; and iteratively updating configuration data, including prompt templates and output ranking parameters, based on the continuous learning signals and the provenance-tracked training examples while deployed base models remain unchanged.

In at least some embodiments, providing the at least one schema-mapped context record to the multi-stage reasoning pipeline may include sequentially generating evaluation and management levels, procedure codes, modifiers, diagnosis codes, and associations between codes based on prior stage outputs.

In at least some embodiments, the method may further include storing, by the at least one processor, the provenance-preserving schema with immutable source lineage identifiers that may include timestamps, source system identifiers, and configuration version tags.

In at least some embodiments, validating the at least one candidate coding output may include executing, by the at least one processor, ruleset-based verification that may include bundling policies, modifier applicability policies, and payer-specific compliance policies.

In at least some embodiments, the method may further include generating, by the at least one processor, the at least one validation rationale object as a machine-readable record that may include at least one rule identifier, at least one evidence reference to a documentation span, and at least one pass/fail indicator.

In at least some embodiments, augmenting the user interface with telemetry and event logging may include capturing, by the at least one processor, timestamps, user role identifiers, and model and prompt version identifiers associated with the user interaction data.

In at least some embodiments, generating the provenance-tracked training examples may include assigning, by the at least one processor, a confidence score to each ground-truth outcome based on the role-based weights and the quality-based weights.

In at least some embodiments, iteratively fusing signals may include incorporating, by the at least one processor, the downstream operational outcomes that may include payer acceptance indicators and denial indicators to produce the continuous learning signals.

In at least some embodiments, iteratively updating the configuration data may include applying, by the at least one processor, a versioned rollout that may include offline replay and canary promotion without redeploying base models.

In at least some embodiments, the method may further include storing, by the at least one processor, the at least one schema-mapped context record and the at least one validation result with version tags to enable deterministic replay of the multi-stage reasoning pipeline and the at least one validation check.

In at least some embodiments, a system may include at least one processor and at least one memory storing instructions that, when executed by the at least one processor, may configure the at least one processor to receive electronic health data and session-level event records from a plurality of electronic resources, where the electronic health data may include structured record data and unstructured documentation text; normalize the electronic health data and the session-level event records into a provenance-preserving schema that may retain source lineage and may include specialty-aware context metadata; provide at least one schema-mapped context record, including the specialty-aware context metadata, to a multi-stage reasoning pipeline implemented with at least one machine learning model, to generate at least one candidate coding output; validate, using at least one validation check, including at least one ruleset-based verification, the at least one candidate coding output to generate at least one validation result; where the at least one validation result may include at least one verified output, at least one validation rationale object, or both; where the at least one validation rationale object may include at least one of: a rule identifier, an evidence reference, or a pass/fail indicator; augment a user interface with telemetry and event logging interaction data to capture user interaction data associated with the at least one candidate coding output, the at least one verified output, or both; generate provenance-tracked training examples by consolidating the user interaction data, the at least one validation result, or both, using a weighted adjudication mechanism that may aggregate multiple inputs according to role-based weights, quality-based weights, or both, to select ground-truth outcomes; where the multiple inputs may include at least one of: the user interaction data, the at least one candidate coding output, the at least one verified output, the at least one validation rationale object, or the at least one schema-mapped context record; and iteratively adapt the multi-stage reasoning pipeline and the at least one validation check by iteratively fusing signals from the multi-stage reasoning pipeline, the at least one validation check, the user interaction data, the provenance-tracked training examples, and downstream operational outcomes to produce continuous learning signals; and iteratively update configuration data, including prompt templates and output ranking parameters, based on the continuous learning signals and the provenance-tracked training examples while deployed base models remain unchanged.

In at least some embodiments, the at least one processor may be configured to provide the at least one schema-mapped context record to the multi-stage reasoning pipeline by sequentially generating evaluation and management levels, procedure codes, modifiers, diagnosis codes, and associations between codes based on prior stage outputs.

In at least some embodiments, the at least one processor may be further configured to store the provenance-preserving schema with immutable source lineage identifiers that may include timestamps, source system identifiers, and configuration version tags.

In at least some embodiments, the at least one processor may be configured to validate the at least one candidate coding output by executing ruleset-based verification that may include bundling policies, modifier applicability policies, and payer-specific compliance policies.

In at least some embodiments, the at least one processor may be further configured to generate the at least one validation rationale object as a machine-readable record that may include at least one rule identifier, at least one evidence reference to a documentation span, and at least one pass/fail indicator.

In at least some embodiments, the at least one processor may be configured to augment the user interface with telemetry and event logging by capturing timestamps, user role identifiers, and model and prompt version identifiers associated with the user interaction data.

In at least some embodiments, the at least one processor may be configured to generate the provenance-tracked training examples by assigning a confidence score to each ground-truth outcome based on the role-based weights and the quality-based weights.

In at least some embodiments, the at least one processor may be configured to iteratively fuse signals by incorporating the downstream operational outcomes that may include payer acceptance indicators and denial indicators to produce the continuous learning signals.

In at least some embodiments, the at least one processor may be configured to iteratively update the configuration data by applying a versioned rollout that may include offline replay and canary promotion without redeploying base models.

In at least some embodiments, the at least one processor may be further configured to store the at least one schema-mapped context record and the at least one validation result with version tags to enable deterministic replay of the multi-stage reasoning pipeline and the at least one validation check.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

The invention claimed is:

1. A method, comprising:

receiving, by at least one processor, electronic health data and session-level event records from a plurality of electronic resources;

wherein the electronic health data comprises structured record data and unstructured documentation text;

normalizing, by the at least one processor, the electronic health data and the session-level event records into a provenance-preserving schema that retains source lineage and comprises specialty-aware context metadata;

providing, by the at least one processor, at least one schema-mapped context record, including the specialty-aware context metadata, to a multi-stage reasoning pipeline implemented with at least one machine learning model, to generate at least one candidate coding output;

validating, by the at least one processor, using at least one validation check, comprising at least one ruleset-based verification, the at least one candidate coding output to generate at least one validation result;

wherein the at least one validation result comprises at least one verified output, at least one validation rationale object, or both;

wherein the at least one validation rationale object comprises at least one of: a rule identifier, an evidence reference, or a pass/fail indicator;

augmenting, by the at least one processor, a user interface with telemetry and event logging interaction data to capture user interaction data associated with the at least one candidate coding output, the at least one verified output, or both;

generating, by the at least one processor, provenance-tracked training examples by consolidating the user interaction data, the at least one validation result, or both, using a weighted adjudication mechanism that aggregates multiple inputs according to role-based weights, quality-based weights, or both, to select ground-truth outcomes;

wherein the multiple inputs comprise at least one of:

the user interaction data, the at least one candidate coding output, the at least one verified output, the at least one validation rationale object, or the at least one schema-mapped context record; and iteratively adapting, by the at least one processor, the multi-stage reasoning pipeline and the at least one validation check by:

iteratively fusing signals from the multi-stage reasoning pipeline, the at least one validation check, the user interaction data, the provenance-tracked training examples and downstream operational outcomes to produce continuous learning signals; and iteratively updating configuration data, comprising prompt templates and output ranking parameters, based on the continuous learning signals and the provenance-tracked training examples while deployed base models remain unchanged.

2. The method of claim 1, wherein providing the at least one schema-mapped context record to the multi-stage reasoning pipeline comprises sequentially generating evaluation and management levels, procedure codes, modifiers, diagnosis codes, and associations between codes based on prior stage outputs.

3. The method of claim 1, further comprising storing, by the at least one processor, the provenance-preserving schema with immutable source lineage identifiers that comprise timestamps, source system identifiers, and configuration version tags.

4. The method of claim 1, wherein validating the at least one candidate coding output comprises executing, by the at least one processor, ruleset-based verification that comprises bundling policies, modifier applicability policies, and payer-specific compliance policies.

5. The method of claim 1, further comprising generating, by the at least one processor, the at least one validation rationale object as a machine-readable record that comprises at least one rule identifier, at least one evidence reference to a documentation span, and at least one pass/fail indicator.

6. The method of claim 1, wherein augmenting the user interface with telemetry and event logging comprises capturing, by the at least one processor, timestamps, user role identifiers, and model and prompt version identifiers associated with the user interaction data.

7. The method of claim 1, wherein generating the provenance-tracked training examples comprises assigning, by the at least one processor, a confidence score to each ground-truth outcome based on the role-based weights and the quality-based weights.

8. The method of claim 1, wherein iteratively fusing signals comprises incorporating, by the at least one processor, the downstream operational outcomes that comprise payer acceptance indicators and denial indicators to produce the continuous learning signals.

9. The method of claim 1, wherein iteratively updating the configuration data comprises applying, by the at least one processor, a versioned rollout that comprises offline replay and canary promotion without redeploying base models.

10. The method of claim 1, further comprising storing, by the at least one processor, the at least one schema-mapped context record and the at least one validation result with version tags to enable deterministic replay of the multi-stage reasoning pipeline and the at least one validation check.

11. A system, comprising:

at least one processor; and at least one memory storing instructions that, when executed by the at least one processor, configure the at least one processor to:

receive electronic health data and session-level event records from a plurality of electronic resources;

wherein the electronic health data comprises structured record data and unstructured documentation text;

normalize the electronic health data and the session-level event records into a provenance-preserving schema that retains source lineage and comprises specialty-aware context metadata;

provide at least one schema-mapped context record, including the specialty-aware context metadata, to a multi-stage reasoning pipeline implemented with at least one machine learning model, to generate at least one candidate coding output;

validate, using at least one validation check, comprising at least one ruleset-based verification, the at least one candidate coding output to generate at least one validation result;

wherein the at least one validation result comprises at least one verified output, at least one validation rationale object, or both;

wherein the at least one validation rationale object comprises at least one of: a rule identifier, an evidence reference, or a pass/fail indicator;

augment a user interface with telemetry and event logging interaction data to capture user interaction data associated with the at least one candidate coding output, the at least one verified output, or both;

generate provenance-tracked training examples by consolidating the user interaction data, the at least one validation result, or both, using a weighted adjudication mechanism that aggregates multiple inputs according to role-based weights, quality-based weights, or both, to select ground-truth outcomes;

wherein the multiple inputs comprise at least one of:

the user interaction data, the at least one candidate coding output, the at least one verified output, the at least one validation rationale object, or the at least one schema-mapped context record; and iteratively adapt the multi-stage reasoning pipeline and the at least one validation check is configured to:

iteratively fuse signals from the multi-stage reasoning pipeline, the at least one validation check, the user interaction data, the provenance-tracked training examples, and downstream operational outcomes to produce continuous learning signals; and iteratively update configuration data, comprising prompt templates and output ranking parameters, based on the continuous learning signals and the provenance-tracked training examples while deployed base models remain unchanged.

12. The system of claim 11, wherein the at least one processor is configured to provide the at least one schema-mapped context record to the multi-stage reasoning pipeline by sequentially generating evaluation and management levels, procedure codes, modifiers, diagnosis codes, and associations between codes based on prior stage outputs.

13. The system of claim 11, wherein the at least one processor is further configured to store the provenance-preserving schema with immutable source lineage identifiers that comprise timestamps, source system identifiers, and configuration version tags.

14. The system of claim 11, wherein the at least one processor is configured to validate the at least one candidate coding output by executing ruleset-based verification that comprises bundling policies, modifier applicability policies, and payer-specific compliance policies.

15. The system of claim 11, wherein the at least one processor is further configured to generate the at least one validation rationale object as a machine-readable record that comprises at least one rule identifier, at least one evidence reference to a documentation span, and at least one pass/fail indicator.

16. The system of claim 11, wherein the at least one processor is configured to augment the user interface with telemetry and event logging by capturing timestamps, user role identifiers, and model and prompt version identifiers associated with the user interaction data.

17. The system of claim 11, wherein the at least one processor is configured to generate the provenance-tracked training examples by assigning a confidence score to each ground-truth outcome based on the role-based weights and the quality-based weights.

18. The system of claim 11, wherein the at least one processor is configured to iteratively fuse signals by incorporating the downstream operational outcomes that comprise payer acceptance indicators and denial indicators to produce the continuous learning signals.

19. The system of claim 11, wherein the at least one processor is configured to iteratively update the configuration data by applying a versioned rollout that comprises offline replay and canary promotion without redeploying base models.

20. The system of claim 11, wherein the at least one processor is further configured to store the at least one schema-mapped context record and the at least one validation result with version tags to enable deterministic replay of the multi-stage reasoning pipeline and the at least one validation check.

* * * * *